United States Patent [19]

Smith et al.

[11] Patent Number: 5,331,100
[45] Date of Patent: Jul. 19, 1994

[54] SELF-BUILDING DETERGENTS

[75] Inventors: Harry A. Smith; Donald A. Tomalia, both of Midland, Mich.

[73] Assignee: Dowbrands Inc., Indianapolis, Ind.

[21] Appl. No.: 125,912

[22] Filed: Nov. 27, 1987

[51] Int. Cl.$^5$ ............................................. C07C 231/10
[52] U.S. Cl. .................................................... 564/468
[58] Field of Search ...................... 260/404.5; 564/468

[56] References Cited

U.S. PATENT DOCUMENTS

| | | | |
|---|---|---|---|
| 2,117,207 | 5/1938 | Orthner | 260/404.5 |
| 4,374,056 | 2/1983 | Watanabe et al. | 562/565 |
| 4,454,060 | 6/1984 | Lai et al. | 252/547 |
| 4,743,388 | 5/1988 | Lega | 260/404.5 |

FOREIGN PATENT DOCUMENTS

| | | | |
|---|---|---|---|
| 972245 | 8/1975 | Canada . | |
| 48-315 | 1/1973 | Japan . | |
| 49-12118 | 2/1974 | Japan . | |
| 51-36411 | 3/1976 | Japan | 260/404.5 |
| 53-31618 | 3/1978 | Japan | 260/404.5 |
| 615062 | 4/1978 | U.S.S.R. | 260/404.5 |
| 1404054 | 9/1972 | United Kingdom . | |

*Primary Examiner*—José G. Dees
*Assistant Examiner*—Joseph M. Conrad

[57] ABSTRACT

Self-building laundry detergents are organic polyamine amides, which contain a plurality of carboxylate radicals and an amide ester. These compounds are useful individually as detergents or as components in detergent compositions.

10 Claims, No Drawings

SELF-BUILDING DETERGENTS

BACKGROUND OF THE INVENTION

This invention relates to self-building detergents and a method for their preparation.

Self-building detergents are useful in clothes cleaning, dish cleaning and the like.

Detergents and soaps precipitate out of aqueous solution if certain ions, such as calcium or magnesium, are present in high concentrations. Water with these ions present in sufficiently high amounts is known as hard water. Chelating agents are compounds which complex these detrimental ions in such a way that the ions are no longer available to cause the precipitation of detergents and soaps. It is known to use certain chelating agents called builders in conjunction with detergents and soaps to minimize or eliminate problems associated with their use in hard water.

Builders which have been used include phosphates, carbonates, borates, silicates and citrates. Problems existing with conventional builders include ecological contamination in some cases and lack of effectiveness in others. In addition, various problems exist with the use of separate detergent(s) and/or soap(s) with builders, such as separation of particles in the particulate cleaning powder before being mixed with water.

Mechanisms exist to circumvent the problems associated with using a separate builder. These mechanisms include depositing the builder and soap(s) and/or detergent(s) in a single particle or dissolving the builder and soap(s) and/or detergent(s) in a concentrated solution. However, component incompatibility, consumer preference for solid cleaning systems, breakdown of bleaching agents and high cost are factors which encourage a search for additional approaches to address these problems. One answer is to use a selfbuilding detergent which is a molecule which acts as a detergent as well as a builder. British Patent 1,404,054 describes a group of such self-building detergents. However, these self-building detergents disadvantageously have poor cleaning ability for cleaning clothes. Thus, what is needed is an effective self-building detergent which has good detergency over a wide range of water hardness.

SUMMARY OF THE INVENTION

The present invention is a class of polyamine amides which contains one or more amide ester radicals and a plurality of amine radicals in which the aforementioned nitrogen atoms are connected by a plurality of divalent organic radicals, provided that
 (1) each amine nitrogen is bonded to at least one divalent lower aliphatic radical terminated with carboxylate substituent;
 (2) each amine nitrogen is not bonded to a hydrogen radical; and
 (3) the amide ni trogen is bonded to one hydrogen radical.

In another aspect, this invention is a process for the preparation of the polyamine amides which comprises following the steps of
 (A) contacting an organic acid and a polyamine under conditions sufficient to form water;
 (B) removing at least a portion of the water formed in Step A; and
 (C) contacting the dewatered product with a second reactant to substitute all remaining amino hydrogen atoms with alkyl carboxylate substituents thereby forming the carboxylated polyamine amide.

These polyamine amides are self-building detergents useful for cleaning, particularly clothes cleaning. It is surprising how effective these polyamine amides are as detergents and builders.

DETAILED DESCRIPTION OF ILLUSTRATIVE EMBODIMENTS

Preferably, the polyamine amides of this invention are of the formula

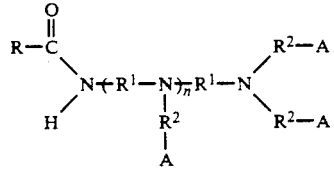

wherein R is a monovalent organic radical, $R^1$ is, separately in each occurrence, a divalent organic radical, $R^2$, is separately in each occurrence, a divalent lower aliphatic radical, n is the number of repeating groups and A is, in each occurrence, selected from the group consisting of

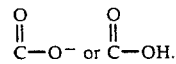

Preferably, $R^2$ contains 1 or 2 carbon atoms; more preferably, $R^2$ is $-CH_2-$ or $-CH_2-CH_2-$; and most preferably, is $R^2$ is $-CH_2-CH_2-$. Preferably, $R^1$ contains to about 6 carbon atoms and more preferably, $R^1$ contains 2 to about 4 carbon atoms. Preferably, R contains from 1 to about 30 carbon atoms. More preferably R contains from about 11 to about 20 carbon atoms and most preferably, R contains from about 13 to about 18 carbon atoms. Preferably, A is

When A is

the polyamine amide is in the salt form. The polyamine amide salt counterions are preferably selected from the group consisting of metal ions, ammonium ions and phosphonium ions. It is preferred that the counterions are lithium, sodium, potassium, ammonium or substituted ammonium ions. It is more preferred that the counterion is a sodium ion.

These polyamine amides may be used as conventional detergents in conventional processes such as clothes laundering, dish cleaning and the like. In a preferred embodiment, these polyamine amides are used in clothes laundering. The polyamine amides may be used individually or two or more polyamine amides may be used in blends although it is preferred to use the polyamine amides individually. The polyamine amides may be used alone as detergents or may be further mixed with various additives such as additional chelating agents and nonionic surfactants to form a detergent composition. Examples of chelating agents which may be mixed with the compounds of this invention include ethylenediaminetetraacetic acid and salts or derivatives thereof such as Versenol 120 which is a registered trademark of The Dow Chemical Company for a concentrated solution of the trisodium salt of N-(carboxymethyl)-N'-(2-hydroxyethyl)-N,N'-ethylene-diglycine. When very basic chelating agents such as Versenol 120 are usedr it may be desirable to also use an agent to balance the basicity such as a crystalline silicate. Sodium metasilicate is an example of a silicate useful for this purpose. Nonionic surfactants which may be mixed with the compounds of this invention to form detergent compositions include the reaction product of one mole of a C10 to C30 fatty alcohol reacted with 3 to 40 moles of ethylene oxide. An example of a nonionic surfactant useful in the practice of this invention is Tergitol 15-S-9 which is a registered trademark of the Union Carbide Corporation for the reaction product of a $C_{11-15}$ fatty alcohol with nine moles of ethylene oxide.

In a preferred embodiment, the compounds of this invention are used in a detergent composition. Such compositions may include a chelating agent, an agent such as sodium metasilicate to balance the basicity of the chelating agent or a nonionic surfactant or any combination thereof in addition to the compound of this invention. The detergent composition preferably comprises from about 0 to about 60 weight percent chelating agent; from about 0 to about 10 weight percent sodium silicate; from about 0 to about 30 weight percent nonionic surfactant; and the remainder being the compound of this invention. It is more preferred that the detergent composition comprises from about 5 to about 25 weight percent chelating agent; from about 1 to about 5 weight percent sodium silicate; from about 5 to about 30 weight percent nonionic surfactant; and the remainder being the compound of this invention. It is preferred that Versenol 120 be used as the chelating agent and that Tergitol 15-S-9 be used as the nonionic surfactant.

Any amount of detergent which will result in cleaning is useful in the practice of this invention. Preferably from about 0.2 weight percent up to about 3.0 weight percent of detergent in water is used. This invention may be practiced at any temperature and pressure at which cleaning will take place. Typical cleaning temperatures are between about 4° C. and about 90° C. Cleaning operations are generally conducted at or near atmospheric pressures, for economic reasons, though elevated or reduced pressures may be employed.

The level of cleaning obtained using the compounds of this invention varies depending on factors such as the amount of detergent used, temperature, additives present and water hardness. Good detergency may be obtained using the compounds of this invention alone. The detergency of the compounds of this invention is not detrimentally affected by water hardness up to about 1000 ppm and actually increases between distilled water and 150 ppm calcium. The compounds of this invention are effective as detergents at temperatures ranging from about the low temperature (around 4° C.) and high temperature (about 90° C.) typically used in clothes laundering.

The polyamine amides of this invention are prepared by a process comprising reacting an organic acid with a polyamine, stripping off the water formed thereby, and contacting the dewatered product with a second reactant to substitute all remaining amino hydrogen atoms with alkyl carboxylate substituents thereby forming the carboxylated polyamine amide.

Organic acids useful in the process of this invention include organic compounds containing at least one carboxylate radical. Typically, the organic acids contain from 1 to about 100 carbon atoms. Preferably, the organic acids contain more than about 4 carbon atoms and more preferably, more than about 13 carbon atoms. Preferably, the organic acids contain less than about 50 carbon atoms and more preferably less than about 21 carbon atoms. Most preferably, the organic acids contain between about 14 and about 19 carbon atoms. Preferably the organic acids contain fewer than 3 carboxylate radicals and most preferably fewer than 2 carboxylate radicals. Examples of preferred organic acids include palmitic acid, stearic acid, myristic acid and oleic acid.

The polyamines useful in practicing this invention are preferably of the formula

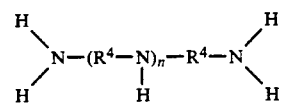

in which $R^4$ is independently a divalent organic radical and n is the number of repeating moieties. $R^4$ preferably contains from 2 to about 15 carbon atoms, more preferably $R^4$ has fewer than about 10 carbon atoms. $R^4$ more preferably has fewer than about 5 carbon atoms and most preferably has fewer than about 4 carbon atoms; n is preferably less than 100, more preferably is less than about 20, even more preferably less than about 5 and most preferably is 1. It is preferred to use diethylerietriamine.

The organic acid and polyamine are contacted under conditions sufficient to form water. The reactants can be added in any amounts and order. It is preferred to use the polyamine in an amount from stoichiometric up to a slight excess. The polyamine is more preferably present in an amount from stoichiometric up to an excess of about 10 weight percent. The reacting mixture can be in any container which will contain the reactants and allow the desired temperature and pressure to be applied. The temperature and pressure of contact depend on many factors such as reactants used, solvent if any and the like. Typical temperatures range between about 50° C. and about 200° C. Preferably, the temperature is above about 110° C., more preferably above about 140° C. Preferably, the temperature is below about 170° C. The pressure is sufficient to keep at least part of the reactants in the liquid phase. Most preferable pressure is atmospheric. The combination of pressure and temperature must be sufficient to allow the reaction mixture to reflux. The reaction is allowed to proceed until the desired degree of completion is reached. Preferably, the reaction is allowed to proceed until at least about 80 percent of the reactants have been converted to product, more preferably until at least about 90 percent of the reactants have been converted to product. Typical reaction times range between about 3 and about 8 hours.

Preferably, the reaction proceeds in an inert, water azeotroping solvent. The solvent typically comprises between about 1 and about 20 weight percent of the reacting system. Preferably, the solvent comprises less than about 5 weight percent of the reaction system. Preferably, the solvent comprises more than about 2 weight percent of the reacting system. Preferably, the solvent is immiscible with water. It is preferred that the solvent is toluene, xylene, benzene, methylene chloride or a mixture thereof. In a preferred embodiment, the solvent forms an azeotrope with the water formed in the reaction and the water is removed by azeotropic distillation.

The dewatered product, a polyamine amide, is next contacted with a second reactant selected from the group consisting of unsaturated esters, amides, nitriles and carboxylic acids to form a carboxylated polyamine amide. It is preferred that the second reactant be an unsaturated ester. It is more preferred that the second reactant be methyl acrylate, dimethyl maleate or dimethyl fumarate.

Any relative amounts of the polyamine amide and the second reactant which will react are useful in the practice of this invention. It is preferred to use approximately stoichiometric amounts of the reactants. That is, if the polyamine amide has x number of amine nitrogens available to be substituted with the carboxylate group, then x moles of the second reactant are used per mole of the polyamine amide.

The contact of the second reactant and the polyamine amide may be conducted at any temperature and pressure at which the reaction will occur. While superatmospheric and subatmospheric pressures are operable, it is preferred to conduct the reaction at atmospheric pressure for the sake of convenience. It is preferred that the reaction take place at a temperature of at least 30° C. and more preferred that the temperature be at least about 45° C. It is preferred that the reaction take place at a temperature of no greater than about 70° C. and more preferred that the temperature be no greater than about 55° C.

The reaction is allowed to proceed until a desired degree of conversion of the polyamine amide to carboxylated polyamine amide is obtained. It is preferred that at least about 50 percent of the polyamine amide reacts. It is more preferred that at least about 70 percent reacts and most preferred that at least about 90 percent reacts. It is preferred that the selectivity to the carboxylated polyamine amide is at least about 99 percent. It is preferred that the reaction proceed for no more than about 24 hours and more preferred that it proceed for no more than about 20 hours. It is preferred that the reaction proceed for at least about 8 hours.

The contact of the second reactant and the polyamine amide preferably takes place in the presence of a solvent in sufficient amount to make the system fluid. The amount of solvent is preferably about 50 weight percent of the reaction mixture. Preferred solvents are lower aliphatic alcohols such as for example, methanol, ethanol, propanol, butanol, pentanol and hexanol. It is more preferred to use methanol as the solvent.

The carboxylated polyamine amide so prepared is subjected to hydrolysis in the presence of water and a base. Examples of bases useful in the process include NaOH, KOH, $Na_2CO_3$ and $K_2CO_3$. It is preferred to use NaOH. The relative amount of base to carboxylated polyamine amide is any which will result in the conversion of the carboxylated polyamine amide to the salt form. It is preferred that the ratio of equivalents of base to equivalents of carboxylated polyamine amide be greater than 1. It is more preferred that the ratio be at least about 1.05:1 and no greater than about 1.15:1. It is preferred that the hydrolysis take place at a temperature of at least 25° C. and more preferred that the temperature be at least about 45° C. It is preferred that the reaction take place at a temperature of no greater than about 70° C. and more preferred that the temperature be no greater than about 60° C. While superatmospheric and subatmospheric pressures are operable, it is preferred to conduct the hydrolysis at atmospheric pressure for the sake of convenience.

The hydrolysis is allowed to proceed until a desired conversion of the carboxylated polyamine amide to the salt form is obtained. It is preferred that at least about 80 percent of the carboxylated polyamine amide is converted to the salt form and more preferred that at least about 90 percent is converted.

The following examples are provided to further illustrate the invention and are not to be construed as limiting the invention in any way. Unless otherwise stated, all parts and percentages are given by weight.

Example 1

Preparation of the Sodium Salt of Oleic Amide of Diethylenetriamine Tripropionate A mixture of 141.2 g (0.50 mole) of oleic acid and 51.6 g (0.50 mole) of diethylenetriamine in 0.100 liter of toluene is heated to reflux. The mixture is allowed to reflux until no more water is generated as detected by formation of the water toluene azeotrope. This takes about 6 to 8 hours. The toluene is stripped by distillation at 50° C.–100° C. and at about 200 mm of mercury. The residue is dissolved in 0.300 liter of methanol. To this solution 172.7 g (2.00 moles) of methyl acrylate is added. This new solution is heated to 50° C. and kept at 50° C. for 16 hours. The product is flash distilled to remove the methanol and unreacted methyl acrylate. To this residue is added 66 g of NaOH in 100 ml of water and 400 ml of methanol. This solution is heated 6 hours at 50° C. Stripping off the water and methanol leaves 346.6 g of a solid. Infrared and nuclear magnetic resonance analyses show the solid is 91.5 percent sodium salt of oleic amide of diethylenetriamine triamine tripropionate. The remainder is essentially water and methanol.

The product as prepared is used to make a 0.1 weight percent aqueous solution. This solution has a pH of 10.8 and a surface tension as determined by a DuNoy's tensionmeter, of 33.9 dynes/cm. A 0.100-liter aliquot of a 1 weight percent aqueous solution of the product is titrated with 1 weight percent $CaCl_2$ aqueous solution until a precipitate forms. This titration shows a calcium tolerance equivalent to 3310 ppm $CaCO_3$.

A 0.200-liter aliquot of a 0.05 weight percent aqueous solution is whipped at high speed in a 1-quart Waring[200] blender for 2 minutes. The initial foam and liquid heights are 7.5 cm and 0.0 cm, respectively. After sitting for 5 minutes at room temperature and pressure, the foam and liquid heights are 4.6 cm and 3.2 cm.

EXAMPLES 2–8

Example 1 is repeated except using different fatty acids in place of oleic acid. The test results are shown in Table I.

TABLE I

| Fatty Acid | pH | ST[1] | Foam Test[3] | | Ca tol[2] (ppm CaCO) |
|---|---|---|---|---|---|
| | | | Initial | after 5 min | |
| hexanoic | 10.1 | 47.0 | 5.3/0 | 0.2/5.1 | <5,400 |
| decanoic | 9.4 | 22.1 | 6.7/0 | 2.7/3.7 | 1,565 |

TABLE I-continued

| Fatty Acid | pH | ST[1] | Foam Test[3] Initial | Foam Test[3] after 5 min | Ca tol[2] (ppm CaCO) |
|---|---|---|---|---|---|
| palmitic | 10.1 | 36.9 | 6.1/0 | 2.3/3.7 | 2,160 |
| stearic | 10.0 | 41.0 | 8.1/0 | 6.3/1.6 | 2,785 |
| oleic | 10.8 | 33.9 | 7.5/0 | 4.6/3.2 | 3,310 |
| tallow | 9.9 | 39.1 | 6.4/0 | 2.8/3.4 | 1,865 |
| tall oil | 10.3 | 35.9 | 6.3/0 | 2.7/3.5 | 2,155 |

[1] surface tension in dynes/cm.
[2] calcium tolerance
[3] see Example 1 for explanation These results show the extremely high calcium tolerance of these self-building detergents, particularly those derived from the $C_6$ and $C_{18}$ fatty acids. The excellent foam height and stability obtained using the self-building detergents derived from $C_{18}$ fatty acids is also demonstrated. The results also show the varying properties different compositions possess in aqueous solutions.

General Procedure for Measuring the Cleaning Obtained Using Particular Detergents The effectiveness of self-building detergents is measured using a device called a Terg-O-Tometer known in the art and available from United States Testing Co., Inc. This device comprises a base containing a thermostated bath which is used to control the wash temperature. The bath has a heater and can have a cooler attached to it and wash temperatures of from about 40° F. to about 200° F. are available. Four stainless steel, one-liter beakers are immersed in the bath. The washing takes place in these beakers. Each has an agitator whose rate of agitation can be controlled. During these experiments, the agitation rate is 100 cycles per minute. Length of wash cycle can also be controlled and is set at 10 minutes during these experiments.

Standard soiled cloths are also used. These are pieces of 65/35 polyester/cotton cloth which are 3-inch by 4.5-inch rectangles. Unless stated otherwise, the cloths are soiled with a standard dust-sebum soil commercially available from Scientific Services Company.

A Hunter D25-PC2 reflectometer is used to measure the cleaning of the soiled cloth. The percentage of cleaning is determined by measuring the reflectance, L which is the L value on the L, a, b scale, of the original cloth, the soiled cloth and the washed cloth, and using the values so obtained in the following formula $$\% \text{ Detergency} = \frac{L \text{ washed} - L \text{ soiled}}{L \text{ original} - L \text{ soiled}} \times 100$$

The reflectometer is fitted with an ultraviolet filter so that the effects of optical brighteners are excluded and only actual cleaning is measured.

The procedure generally followed is that the Terg-O-Tometer bath is brought to temperature and then the stainless steel beakers are filled with one liter of water of the desired hardness. Water containing 150 ppm (parts per million) $CaCO_3$ is obtained by dissolving a 2:1 mole ratio of $CaCO_3$ and $MgCO_3$ in distilled water saturated with $CO_2$. The hardness is the ppm of $CaCO_3$ equivalent to the total moles of $CaCO_3$ and $MgCO_3$. When this water has come to the desired temperature, the desired amount of detergent is added. The mixture is then agitated for approximately 10 minutes to ensure that the detergent has gone into solution. Four pieces of soiled cloth are then added to each beaker and the agitators are started. After the 10-minute wash cycle, the cloths are hand-rinsed in cold tap water, squeezed to remove most of the water and then air dried on paper towels. When dry, the samples are read on the reflectometer.

Example 9

Effect of Different Soils on Detergency

The detergency of two compounds of this invention is measured following the procedure outlined above. The compounds used are A, the sodium salt of palmitic amide of diethylenetriamine triprionate and B, the sodium salt of oleic amide of diethylenetriamine triproprionate. The percent detergency is measured as explained above. In this experiment, the soil used is a mixture of clay, lampblack and iron oxides with synthetic sebum and the soiled cloth was WKF 20C obtained from Test Fabrics, Inc. The hardness of the water was 150 ppm. The results obtained are shown in Table II below.

EXAMPLE 10

Effect of Different Soils on Detergency

Example 10 is repeated with the only difference being that the soil used is dust-sebum rather than the soil used in Example 10. The results obtained are also shown in Table II below.

TABLE II

| Example | Compound | Temp °F. | Amount Used[1] | % Detergency |
|---|---|---|---|---|
| 9 | A | 120 | 0.3 | 52 |
|   |   |   | 0.5 | 54 |
|   |   |   | 1.0 | 53 |
|   |   |   | 3.0 | 38 |
| 9 | B | 120 | 0.3 | 50 |
|   |   |   | 0.5 | 54 |
|   |   |   | 1.0 | 60 |
|   |   |   | 3.0 | 50 |
| 10 | A | 120. | 0.3 | 56 |
|   |   |   | 0.5 | 60 |
|   |   |   | 1.0 | 64 |
|   |   |   | 3.0 | 70 |
| 10 | B |   | 0.3 | 58 |
|   |   |   | 0.5 | 62 |
|   |   |   | 1.0 | 67 |
|   |   |   | 3.0 | 74 |

[1] Weight percent of detergent in water

The data shown above indicates that the compounds of this invention show better detergency when the soil used is a dust-sebum mixture more typical of household dirt, rather than the mixture of clay, lamp-black and iron oxides with synthetic sebum. The latter soil mixture is useful for ranking detergents since none are totally effective in romoving it. Further, the data shows that an acceptable level of cleaning is obtained using the low levels of detergent, i.e. less than 0.5 weight percent, normally used in clothes laundering.

EXAMPLE 11

Effect of Water Hardness

The effect of water hardness is measured following the general procedure set forth above. The water temperature used is 120° F. and the soil is dustsebum. The compounds tested were A and B from Examples 10 and 11 and C, the sodium salt of stearic amide of diethylenetriamine triproprionate. The results obtained are shown in Table III below.

TABLE III

| Compound | Hardness (CaCO$_3$ ppm) | % Detergency |
|---|---|---|
| A | 10 | 32 |
|   | 150 | 57 |
|   | 300 | 58 |
| B | 10 | 36 |
|   | 150 | 60 |
|   | 300 | 57 |
| C | 10 | 36 |
|   | 150 | 46 |
|   | 300 | 47 |

The data shown in Table III above shows that the compounds of this invention are effective over a relatively wide range of water hardness.

Example 12

Effect of Chelating Agents as Additives

The effect of using a mixture of the sodium salt of oleic amide of diethylenetriamine triprionate with Versenol 120, a registered trademark of The Dow Chemical Company for a concentrated solution of the trisodium salt of N-(carboxymethyl)-N'-(2-hydroxyethyl)-N,N'-ethylenediglycine was measured in a process following the procedure outlined above where the wash is conducted at 120° F. and the soil used is the standard dust-sebum mixture.

TABLE IV

| Mixture (C$_{18}$/Versenol 120)[1] | C$_{18}$ (Wt %) | % Detergency |
|---|---|---|
| 100/0 | 0.3 | 59 |
|  | 0.5 | 61 |
|  | 1.0 | 65 |
|  | 3.0 | 75 |
| 50/50 | 0.3 | 92 |
|  | 0.5 | 93 |
|  | 1.0 | ≧93 |
|  | 3.0 | ≧93 |
| 75/25 | 0.3 | 93 |
|  | 0.5 | 93 |
|  | 1.0 | 93 |
|  | 3.0 | 93 |

[1] Weight ratio of the two ingredients

The data shown in Table IV above demonstrates the increased detergency of the sodium salt of oleic amide of diethylenetriamine triprionate when mixed with a trisodium salt of N-(carboxymethyl)-N'-(2-hydroxyethyl)-N,N'-ethylenediglycine. This demonstrates the effectiveness of the oleic derivative as a component in a formulated detergent system.

Example 13

Effect of Sodium Metasilicate Additive

Example 13 demonstrates the enhanced detergency obtained by using a mixture of the oleic derivative with Versenol 120. This example measures the effect of adding sodium metasilicate to the formulation used in Example 13. Otherwise, the same conditions are used. The results are given in Table V below.

Example 14

Effect of Sodium Metasilicate Additive

Example 14 is repeated with the only difference being that the temperature used is 60° F. rather than 120° F. These results are also given in Table V below.

TABLE V

| Formulation C$_{18}$/Versenol/Sodium Silicate[1] | Temp (°F.) | Detergent (Wt %) | % Detergency |
|---|---|---|---|
| 40/10/5 | 120 | 0.3 | 47 |
|  |  | 0.5 | 90 |
|  |  | 1.0 | 92 |
|  |  | 3.0 | 92 |
| 40/10/5 | 60 | 0.3 | 46 |
|  |  | 0.5 | 84 |
|  |  | 1.0 | 91 |
|  |  | 3.0 | 92 |
| 40/40/1 | 120 | 0.3 | 54 |
|  |  | 0.5 | 80 |
|  |  | 1.0 | 92 |
|  |  | 3.0 | 92 |
| 40/40/1 | 60 | 0.3 | 57 |
|  |  | 0.5 | 84 |
|  |  | 1.0 | 90 |
|  |  | 3.0 | 92 |
| 40/40/5 | 120 | 0.3 | 58 |
|  |  | 0.5 | 91 |
|  |  | 1.0 | 92 |
|  |  | 3.0 | 92 |
| 40/40/5 | 60 | 0.3 | 79 |
|  |  | 0.5 | 90 |
|  |  | 1.0 | 92 |
|  |  | 3.0 | 92 |

[1] Weight ratios of components

The data in Table V indicate that a detergent formulation comprising compound B with sodim meta-silicate and Versenol 120 is a highly effective detergent. This data along with the data in Table IV demonstrates the usefulness of the compounds of this invention in various detergent formulations.

Example 15

Effect of Nonionics as Additives

Example 16 uses the conditions described for Example 14 which include temperature of 120° C. and water hardness of 150 ppm CaCO$_3$, with the only difference being the addition of a nonionic surfactant, Tergitol 15-S-9, to the detergent composition. The first detergent composition, CNSLV, comprises 53 weight percent of the sodium salt of oleic amide of diethylenetriamine triprionate, 15 weight percent of Versenol, 8 weight percent of sodium metasilicate, and 20 weight percent of Tergitol 15-S-9. The second detergent composition, CNSHV, comprises 28 weight percent of the sodium salt of oleic amide of diethylenetriamine triprionate, 50 weight percent of Versenol, 8 weight percent of sodium metasilicate, and 15 weight percent of Tergitol 15-S-9. The percent detergency obtained using these detergent compositions is shown in Table VI below.

TABLE VI

| Detergent Composition | Wt % C$_{18}$ | % Detergency |
|---|---|---|
| CNSLV | 0.025 | 65 |
|  | 0.05 | 75 |
|  | 0.10 | 89 |
|  | 0.15 | 91 |
|  | 0.20 | 94 |
| CNSHV | 0.025 | 82 |
|  | 0.05 | 92 |
|  | 0.10 | 93 |
|  | 0.15 | 93 |
|  | 0.20 | 94 |

The data shown above indicates that the addition of the nonionic surfactant to the detergent composition results in a high level of detergency being obtained while using a low level of detergent which is comparable to the level of detergent used in actual conditions.

We claim:

1. A process for the preparation of a carboxylated polyamine amide having one secondary amide comprising (A) contacting a carboxylic acid and a polyamine, the polyamine of the formula

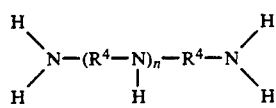

in which $R^4$ is independently a divalent organic radical having from 2 to 15 carbon atoms and n is from 1 to 99, under conditions sufficient to form water and a polyamine amide having one secondary amide;

(B) removing at least a portion of the water formed in Step A; and (C) contacting the dewatered product with an unsaturated ester to substitute all remaining amino hydrogen atoms with alkyl carboxylate substituents thereby forming the carboxylated polyamine amide having one secondary amide.

2. The process of claim 1 wherein the polyamine is diethylenetriamine.

3. The process of claim 1 wherein the unsaturated ester is selected from the group consisting of methyl acrylate, dimethyl maleate and dimethyl fumarate.

4. The process of claim 1 wherein the organic acid and polyamine are contacted at atmospheric pressure and at a temperature above at least about 110° C. and below about 170° C.

5. The process of claim 1 wherein the organic acid and polyamine are contacted in the presence of a solvent which forms an azeotrope with water.

6. The process of claim 5 wherein the solvent is selected from the group consisting of toluene, xylene, benzene, methylene chloride or mixtures thereof.

7. The process of claim 1 wherein the polyamine amide and the second reactant are contacted at atmospheric pressure and at a temperature greater than about 45° C. and less than about 60° C.

8. The process of claim 1 wherein the polyamine amide and the second reactant are contacted in the presence of a solvent.

9. The process of claim 8 wherein the solvent is a lower aliphatic alcohol.

10. The process of claim 1 wherein the polyamine amide and the second reactant are used in stoichiometric amounts.

* * * * *